US012622860B2

(12) United States Patent
Burtt

(10) Patent No.: US 12,622,860 B2
(45) Date of Patent: May 12, 2026

(54) KITS AND METHODS OF USING ASCORBATES TO MODIFY POLYSACCHARIDE FILLERS AND DELIVERY SYSTEMS

(71) Applicant: Advanced Aesthetic Technologies, Inc., Brookline, MA (US)

(72) Inventor: Richard Burtt, Charlestown, MA (US)

(73) Assignee: Advanced Aesthetic Technologies, Inc., Brookline, MA (US)

( * ) Notice: Subject to any disclaimer, the term of this patent is extended or adjusted under 35 U.S.C. 154(b) by 327 days.

(21) Appl. No.: 17/125,572

(22) Filed: Dec. 17, 2020

(65) Prior Publication Data

US 2021/0228468 A1     Jul. 29, 2021

Related U.S. Application Data

(62) Division of application No. 16/097,941, filed as application No. PCT/US2017/039506 on Jun. 27, 2017, now abandoned.

(60) Provisional application No. 62/355,086, filed on Jun. 27, 2016.

(51) Int. Cl.

| | |
|---|---|
| *A61K 8/73* | (2006.01) |
| *A61K 8/60* | (2006.01) |
| *A61K 8/67* | (2006.01) |
| *A61K 9/06* | (2006.01) |
| *A61L 27/20* | (2006.01) |
| *A61L 27/50* | (2006.01) |
| *A61L 27/58* | (2006.01) |
| *A61Q 19/08* | (2006.01) |

(52) U.S. Cl.
CPC .................. *A61K 8/73* (2013.01); *A61K 8/60* (2013.01); *A61K 8/676* (2013.01); *A61L 27/20* (2013.01); *A61L 27/50* (2013.01); *A61L 27/58* (2013.01); *A61Q 19/08* (2013.01); *A61K 9/06* (2013.01); *A61K 2800/882* (2013.01); *A61K 2800/91* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 2007/0037776 | A1 | 2/2007 | Richardson et al. |
| 2009/0143331 | A1 | 6/2009 | Stroumpoulis et al. |
| 2015/0232581 | A1 | 8/2015 | Forget et al. |
| 2016/0038635 | A1 | 2/2016 | Matteuzzi |
| 2019/0110974 | A1 | 4/2019 | Burtt |

FOREIGN PATENT DOCUMENTS

| | | | | |
|---|---|---|---|---|
| EP | 2484387 | A1 | 8/2012 | |
| WO | WO-2015022641 | A2 * | 2/2015 | ............. A61K 8/044 |
| WO | 2015/149946 | A1 | 10/2015 | |
| WO | 2015/155639 | A1 | 10/2015 | |

OTHER PUBLICATIONS

Varoni et al. (Agarose gel as biomaterial for scaffold for implantation surgery: Characterization, histological and histomorphometeric study on soft tissue response), Connective Tissue Research; 53(6), 548-554 (Year: 2012).*

Chandel et al. (Effect of polyethylene glycol on properties and drug encapsulation-release performance of biodegradable/cytocompatible agarose-polyethylene glycol-polycaprolactone amphiphilic co-network gels), American Chemical Society; Materials & Interfaces, (Year: Jan. 13, 2016).*

Cipriani et al. "Wrinkles: Origin and treatment", Advances in cosmetic and dermatology, vol. 2, Issue 1, pp. 1-7 (Year: 2016).*

Bengt et al., Oxidatire Breakdown of Hyaluronic and Chondroitin Sulphuric Acid. Acta Physiologica. Sep. 1943;6(1):37-51.

Fernández-Cossío et al., Biocompatibility of agarose gel as a dermal filler: histologic evaluation of subcutaneous implants. Plast Reconstr Surg. Oct. 2007;120(5):1161-9.

Robertson et al., The degradation of mucins and polysaccharides by ascorbic acid and hydrogen peroxide. Biochem J. Sep. 1941;35(8-9):903-8.

International Search Report and Written Opinion for Application No. PCT/US2017/039506, dated Sep. 25, 2017.

Supplementary European Search Report for Application No. 17821075.3, dated Jun. 18, 2019, 9 pages.

U.S. Appl. No. 16/097,941, filed Oct. 31, 2018, 2019-0110974, Abandoned.

* cited by examiner

*Primary Examiner* — Isis A Ghali

(74) *Attorney, Agent, or Firm* — McCarter & English, LLP; Michael J. DeGrazia

(57) ABSTRACT

Embodiments of the present invention are directed to kits, compositions and methods for modifying and altering polysaccharide fillers and drug delivery systems with the application of an ascorbate.

3 Claims, 1 Drawing Sheet

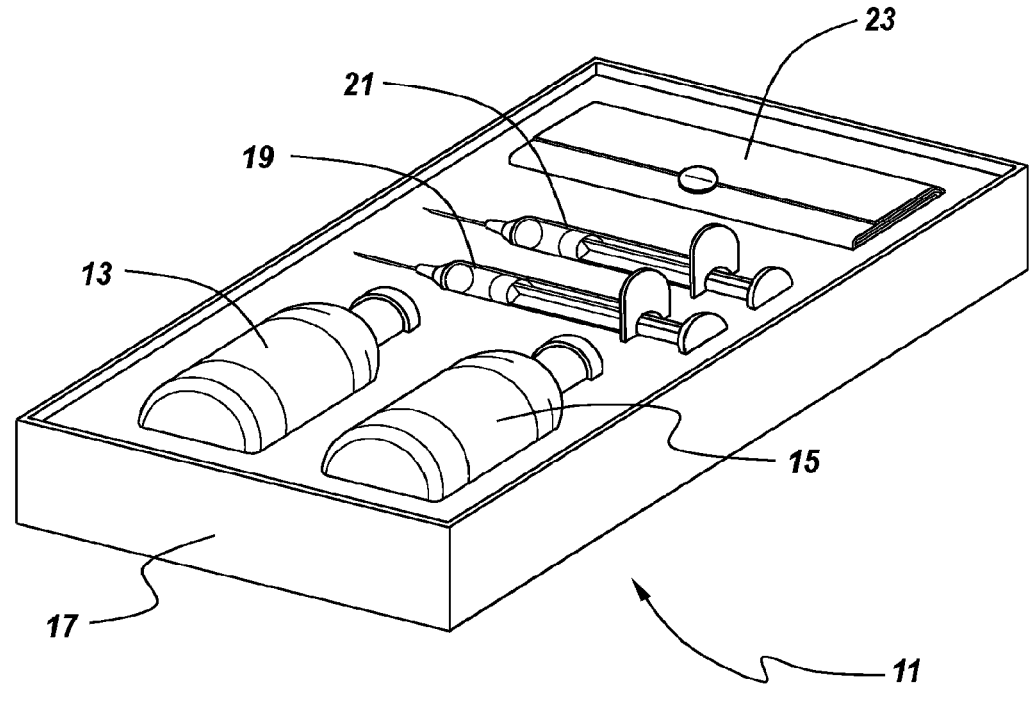

KITS AND METHODS OF USING ASCORBATES TO MODIFY POLYSACCHARIDE FILLERS AND DELIVERY SYSTEMS

RELATED APPLICATION INFORMATION

This application is a divisional of U.S. patent application Ser. No.: 16/097,941, filed Oct. 31, 2018, which is a 371 U.S. National Phase of PCT/US2017/039506, filed Jun. 27, 2017, which claims priority to U.S. Provisional Application No. 62/355,086, filed Jun. 27, 2016. The contents of these applications are incorporated herein by reference in their entirety.

STATEMENT REGARDING FEDERAL FUNDING

Embodiments of the present invention were not conceived or reduced to practice with Federal sponsorship.

BACKGROUND OF THE INVENTION

Polysaccharides are used as cosmetic fillers and as a component of injectable drug delivery systems. When polysaccharides are placed in the body as a filler or as a drug delivery system, the polysaccharides may have a long period of time before such are resorbed into the body through metabolism or other means.

SUMMARY OF THE INVENTION

Embodiments of the present invention facilitate the use of polysaccharides, particularly as such polysaccharides are used as fillers and drug delivery vehicles. Embodiments of the present invention allow the polysaccharide to be modified in vivo or in vitro to impart special physical and chemical properties. For example, without limitation, the physical properties of texture, feel, resistance to pressure, viscosity and the like can be altered or modified, in vivo or in vitro. Similarly, the chemical properties, resistance to degradation and speed, of degradation can be modified or altered.

The modification of physical and chemical features of a polysaccharide used as a filler or drug delivery system allows the health practitioner to modify the filler mass after it has been placed in the body or prior to placement in the body. As used herein, the term, "mass" refers to the polysaccharide material and the surrounding space it occupies. For example, polysaccharide fillers used for cosmetic purposes typically comprise solutions of 1.0 to 5.0%. These solutions may also comprise other materials to improve the flow or feel of the filler, such as hyaluronic acid, and anesthetic agents to address the potential discomfort during the administration of the filler. Anesthetic agents are well known in the art and include, without limitation, lidocaine. These fillers are administered to the deep layer of the skin. An example of a filler of this type is described in PCT/IB2014/060322 to Ghimas SPA, the entire content of which is incorporated herein by reference.

One embodiment of the present invention is directed to a method of altering or modifying a mass comprising a polysaccharide held in the body of an animal. The method comprises the steps of administering an effective amount of ascorbate to the mass. The ascorbate can be administered to the mass prior to the mass being placed in the body or after the mass has been placed in the body.

One embodiment of the method features a polysaccharide having one or more sugars selected from the group consisting of D-galactose and 3,6-anhydro-L-galactopyranose. These sugars are the constituents of agarose. Agarose is used as a dermal filler and as a drug delivery vehicle. As used herein, a "drug delivery vehicle" comprises a polysaccharide and one or more drugs.

As used herein, the term "ascorbate" refers to ascorbic acid and its salts and oxidized forms such as dehydroascorbic acid. Ascorbic acid is commonly known as Vitamin C As used herein, ascorbate refers to both the levo and dextro forms. Ascorbate alters the form of the polysaccharide, increasing its dissolution, breaking down and fluidizing the mass. One embodiment of the present invention features an injectable ascorbic acid, such as Vitamin C As used herein, the term "an effective amount" refers to an amount to cause the polysaccharide to assume a desired fluidized form. The desired fluidized form refers to an more fluid form compared to agarose of same polymer composition and hydration without an ascorbate being present.

Wherein the mass is a delivery vehicle for one or more drugs, the ascorbate has utility to facilitate removal of the polysaccharide, control the delivery or release of drug, address hardness, graininess or nodules in the mass and minimize the mark on the skin from the injection of drug. For example, without limitation, one embodiment of an invention directed to a drug delivery system comprises a polysaccharide and an ascorbate held in a vessel for reconstitution. Upon reconstitution, the ascorbate maintains the polysaccharide in a more fluid state. This fluid may continue after injection of the drug delivery system into a patient. As used herein, the term "drug" is used to refer to any compound or compounds used to effect a biological change or treat a medical condition. The drug may be incorporated into the polysaccharide prior to reconstitution or after reconstitution. Examples of drugs include without limitation, lidocaine, and other anesthetic agents, onabotulinemtoxin A (BOTOX®, Allergan) and other aesthetic agents.

A further embodiment of the present invention is directed to a kit for performing dermal filling procedures or for the administration of drug. The kit comprises a polysaccharide for forming a mass in the body of an animal and an ascorbate for maintaining or making the polysaccharide more fluid for administration to the mass held in the body to effect a modification or speeding the resorption of said mass.

One embodiment of the present kit features a polysaccharide having one or more sugars selected from the group consisting of D-galactose and 3,6-anhydro-L-galactopyranose. These sugars are constituents of the polysaccharide, agarose.

These and other features and advantages will be apparent to those skilled in the art upon viewing the FIGURE which is briefly described below and studying the details description that follows.

BRIEF DESCRIPTION OF THE DRAWINGS

FIG. 1 depicts a kit embodying features of the present invention.

DETAILED DESCRIPTION OF THE INVENTION

Embodiments of the present invention will now be described in detail with respect to a kit for performing dermal filling procedures or for the administration of drug. The present description is directed to embodiments which are considered to be the best mode to practice the present invention at the time of the writing of the present description. Those skilled in the art will recognize that the understanding of the best mode may change in time. Those skilled in the art will also recognize that the features of the present invention described are subject to alteration and modification and such that the present discussion should not be considered limiting.

Turning now to FIG. 1, a kit, generally designated by the numeral 11, embodying features of the present invention is depicted. The term "kit" is used to denote a bundled assembly of parts and constituents for performing a method. The kit 11 comprises two vials, a first vial 13 containing a polysaccharide for forming a mass in the body of an animal and a second vial 15 containing an ascorbate for fluidizing the polysaccharide for administration to the mass held in the body. The first vial 13 and second vial 15 are bundled or held in a package 17 with means for administering the polysaccharide and means for administering the enzyme, in the form of first syringe 19 and second syringe 21, and instructions 23.

The first vial 13 contains a polysaccharide for forming a mass in the body of an animal or patient. The polysaccharide can be pre-made and in a final form ready for administration or be lyophilized for reconstitution with water. The first syringe 19 is used to withdraw the reconstituted or pre-made polysaccharide for injection into an animal or patient. For example, a human subject may use the mass to conceal wrinkles or to build bulk to areas of the body showing signs of atrophy or for which a fuller appearance is desired.

The present kit features a polysaccharide having one or more sugars selected from the group consisting of D-galactose and 3,6-anhydro-L-galactopyranose. These sugars are constituents of the polysaccharide, agarose, which is used as a dermal filler. Agarose is sold as a dermal filler under the mark ALGENESS®.

The second vial 15 contains an ascorbate to effect a modification or speeding the resorption or altering the fluidity of the mass. The ascorbate can be pre-made and in a final form ready for administration or be lyophilized for reconstitution with water. The second syringe 21 is used to withdraw the reconstituted or pre-made ascorbate for injection into the mass. For example, in a human subject using the mass to conceal wrinkles or to build bulk to areas of the body showing signs of atrophy, the subject may desire the mass to have a softer feel, or the mass may exhibit graininess or nodules. The ascobate is placed in the mass and the mass manipulated to distribute the ascorbate where the ascorbate may effect a modification of the polysaccharide. The polysaccharide assumes a more fluid form, capable of faster metabolisation, removing graininess and nodules and presenting a softens the mass. Ascorbic acid is available in injectable forms from numerous suppliers. Mylan Institutional LLC (Rockland, Ill. 61103) sells Ascorbic Acid for Injection 500 mg/ml. The monogram for ascorbic acid suggests that doses of ascorbic acid up to 6 grams are tolerated.

Embodiments of the present invention facilitate the use of polysaccharides, particularly as such polysaccharides are used as fillers and drug delivery vehicles. Embodiments of the present invention allow the polysaccharide to be modified in vivo or in vitro to impart special physical and chemical properties. That is, the ascorbate can be distributed into the polysaccharide prior to administration of the polysaccharide or after administration of the polysaccharide to create a desired physical property of texture, feel, resistance to pressure, viscosity and the like. Similarly, the chemical properties of resistance to degradation and speed of degradation can be modified or altered.

The modification of physical and chemical features of a polysaccharide used as a filler or drug delivery system allows the health practitioner to modify the filler mass after it has been placed in the body or prior to placement in the body. For example, the mass may be fluidized for removal or minimization by withdrawing the mass after the administration of the ascorbate. The fluidization of the mass allows the mass to be redistributed and aids in the resorption of the mass.

The use of the kit 11 and the instructions 23 will now be described with respect to an embodiment of the present invention directed to a method of altering or modifying a mass comprising a polysaccharide held in the body of an animal. The instructions 23 direct the user to reconstitute the polysaccharide held in first vial 13 and the ascorbate held in second vial 15 if reconstitution is needed. The instructions 23 direct the user to administer polysaccaride held in the first vial 13. The instructions 23 further direct the user to administer an effective amount of an ascorbate for the polysaccharide to the mass. The ascorbate can be administered to the mass prior to the mass being placed in the body or after the mass has been placed in the body. More than one application of ascorbate may be used to obtain the desired consistency of the mass. The mass may be gently kneaded or manipulated to distribute the ascorbate throughout the mass structure. The fluidized mass may be manipulated into a desired position or removed by suction through the same syringe administering the ascorbate.

Embodiments of the method and kits feature a polysaccharide having one or more sugars selected from the group consisting of D-galactose and 3,6-anhydro-L-galactopyranose. These sugars are the constituents of agarose. Agarose is used as a dermal filler and as a drug delivery vehicle.

Embodiments of the method and kits features an ascorbate, ascorbic acid, Vitamin C. Ascorbic acid is well tolerates and the amount based on the mass of polysaccharide. Monographs for such enzymes are available from the respective manufacturers and are incorporated herein by reference.

EXAMPLE 1

This example features the use of ascorbic acid to effect a modification of agarose gel. Agarose gel is extruded and placed on a hard working surface. The gel is of the type commonly used as a dermal filler and available under the trademark ALGENESS®. The gel retains the shape of the extrudate, tubular in form. To the extrudate, ascorbic acid in solution (500 mg/ml) is applied. The extrudate exhibits rapid fluidization. With mild agitation, the extrudate form is lost and the gel is totally fluidized. The fluidized gel can be suctioned by needles.

Thus, the present invention has been described in detail with the understanding that the present discussion is subject to modification and alteration without departing from the teaching. Therefore, the present invention should not be limited to the precise details but should encompass the subject matter of the claims that follow and their equivalents.

The invention claimed is:

1. A method of fluidizing an agarose gel mass solely with ascorbic acid, the method consisting of a step of administering in vivo an effective amount of a solution consisting of 500 mg/ml ascorbic acid directly to the to the agarose gel mass to fluidize the agarose gel mass to a desired fluidized form, wherein the ascorbic acid is injectable ascorbic acid, the agarose gel mass is solely fluidized by the ascorbic acid, and the fluidized form can be suctioned by needles.

2. The method of claim 1 wherein said mass is a dermal filler.

3. The method of claim 1 wherein said mass is a delivery vehicle for one or more drugs.

\* \* \* \* \*